United States Patent
Vartanian et al.

(10) Patent No.: US 9,144,478 B2
(45) Date of Patent: Sep. 29, 2015

(54) MULTI-PURPOSE DENTAL BIB

(71) Applicants: Albert Vartanian, Los Angeles, CA (US); Marine Martirosyan, Studio City, CA (US)

(72) Inventors: Albert Vartanian, Los Angeles, CA (US); Marine Martirosyan, Studio City, CA (US)

( * ) Notice: Subject to any disclaimer, the term of this patent is extended or adjusted under 35 U.S.C. 154(b) by 19 days.

(21) Appl. No.: 13/763,839

(22) Filed: Feb. 11, 2013

(65) Prior Publication Data

US 2014/0227660 A1    Aug. 14, 2014

(51) Int. Cl.
*A61C 19/00* (2006.01)
*A41B 13/10* (2006.01)

(52) U.S. Cl.
CPC .............. *A61C 19/00* (2013.01); *A41B 13/103* (2013.01); *A61C 19/002* (2013.01)

(58) Field of Classification Search
CPC ....... A61C 19/00; A41B 13/10; A41B 13/103
USPC ............. 433/136, 137; 2/48, 49.2, 49.4, 49.1; 128/849, 852, 853, 854
See application file for complete search history.

(56) References Cited

U.S. PATENT DOCUMENTS

| | | | | |
|---|---|---|---|---|
| 3,677,266 | A * | 7/1972 | Green | 128/849 |
| 4,553,538 | A * | 11/1985 | Rafelson | 128/852 |
| 4,570,628 | A * | 2/1986 | Neal | 128/853 |
| 5,816,253 | A * | 10/1998 | Sosebee | 128/849 |
| 5,988,172 | A * | 11/1999 | Sosebee | 128/849 |
| 6,000,056 | A * | 12/1999 | Brady et al. | 2/49.1 |
| 6,186,139 | B1 * | 2/2001 | Bezicot et al. | 128/200.24 |
| 6,644,317 | B1 * | 11/2003 | Lawton | 128/849 |
| 6,799,330 | B1 * | 10/2004 | Lansdell | 2/49.4 |
| 7,174,571 | B1 * | 2/2007 | Vonrinteln | 2/49.2 |
| 7,269,855 | B2 * | 9/2007 | LaRocco | 2/49.1 |
| 7,293,654 | B1 * | 11/2007 | Wilson et al. | 206/572 |
| 7,673,754 | B2 * | 3/2010 | Wilson et al. | 206/572 |
| 7,770,583 | B2 * | 8/2010 | Harris et al. | 128/849 |
| 2004/0205876 | A1 * | 10/2004 | Bruffett | 2/49.2 |
| 2005/0144693 | A1 * | 7/2005 | Hagen | 2/49.1 |
| 2006/0169290 | A1 * | 8/2006 | Harris et al. | 128/852 |
| 2011/0197329 | A1 * | 8/2011 | Hillary | 2/49.5 |

* cited by examiner

*Primary Examiner* — Robyn Doan
*Assistant Examiner* — Tatiana Nobrega
(74) *Attorney, Agent, or Firm* — Richard J. Hepner

(57) ABSTRACT

A multi-purpose dental bib, to be worn by a patient during a dental procedure, may incorporate gauze pads into windows and/or pockets integral to the bib. The multi-purpose dental bib may be employed to protect the patient's clothing from liquid and/or solid debris generated during a dental procedure, and to wipe the patient's face and mouth during or at the completion of a dental procedure. The multi-purpose dental bib may additionally be employed to clean dental tools, such as a dental mirror, during a dental procedure by means of the gauze pads incorporated into the windows and/or pockets strategically located on the multi-purpose dental bib.

15 Claims, 4 Drawing Sheets

MULTI-PURPOSE DENTAL BIB

FIELD OF THE INVENTION

The present invention relates generally to the field of dental equipment and supplies, particularly dental bibs. More specifically, the present invention provides a useful and novel dental bib [hereinafter "multi-purpose dental bib"] for cleaning dental instruments as well as for protecting dental patients from debris during dental procedures.

BACKGROUND OF THE INVENTION

Unless specifically indicated otherwise, the materials described in this section are not prior art to the claims in this application, and are not admitted to be prior art by inclusion in this section.

The material in this patent document is subject to copyright protection under the copyright laws of the United States and other countries. The copyright owner grants a limited license to any member of the public to reproduce the patent document as it appears in official governmental records. All other copyright rights are reserved.

A dental bib may have multiple uses in dental practice. Primarily, a dental bib is employed to protect a patient's garments from liquid and/or solid debris generated during a dental procedure. Further, a dental bib may be used to wipe a patient's face and mouth during or at the completion of surgery. Finally, a dental bib may be used by a dentist to clean the liquid and/or solid debris from dental instruments.

Dental bibs may be designed employing a variety of materials, constructions, and features. A prevalent dental bib design comprises an apron in combination with a means of securing the apron in position over the patient's chest.

Typically, dental bibs are disposable, and constructed of one or more absorbent paper plies in combination with a waterproof plastic ply backing. For example, in U.S. Pat. No. 5,930,836, Morris discloses a dental bib suggesting a bib material comprising a layer of paper toweling for absorbency with a plastic film backing for moisture protection. In U.S. Pat. No. 7,836,518, Bloom et al. disclose a dental bib wherein the main body portion comprises an absorbent side and a waterproof side.

Dental bibs may be held in place, generally covering the chest of a patient, by any of a number of means. For example, in U.S. Pat. No. 3,488,773, Stemmer discloses a dental bib comprising a multi-layer paper section backed by a plastic sheet to form a rectangular panel. A pressure-sensitive adhesive, which provides an attachment to the patient's clothing, is disposed on three corners of the plastic back and permits the towel to be disposed over the chest to form a shield. In U.S. Pat. No. 4,646,365, Surprise et al. disclose a disposable bib with an integral, elasticized neckband. U.S. Pat. No. 5,825,849 to Lansing et al. discloses a dental bib holder comprising spring clips mounted at either end of a flexible strap, the flexible strap being positioned about the back of a patient's neck, and the clips being attached to a dental bib. In U.S. Pat. No. 7,540,036, Paulsen discloses a disposable bib that is secured around the neck of the patient via magnets.

One disadvantage inherent to conventional dental bib designs is their limited usefulness for cleaning dental instruments. The paper layer(s) of a conventional dental bib lacks the bulk and softness of texture necessary to clean and/or polish a dental instrument. Due to this disadvantage, a dentist may typically be required to interrupt the dental procedure in order to grasp a piece of gauze, clean and/or polish the dental tool with the piece of gauze, dispose of the piece of gauze, and then resume the dental procedure.

Another disadvantage inherent to conventional dental bib designs is their limited usefulness for capturing solid debris generated during a dental procedure. The paper layer(s) of a conventional dental bid lacks the bulk and/or physical features necessary to capture solid debris. Here, again, a dentist may typically be required to interrupt the dental procedure in order to grasp a piece of gauze, capture the solid debris with the piece of gauze, dispose of the piece of gauze, and then resume the dental procedure.

What is needed is a new dental bib design that combines the capacity of gauze to capture solid debris and to clean and polish dental instruments with the capability of conventional dental bib to protect a patient's garments from liquid debris during a dental procedure.

SUMMARY OF THE INVENTION

In view of the foregoing limitations and disadvantages inherent to the conventional apparatus in the related art, the present invention provides a useful and novel multi-purpose dental bib for protecting a patient's garments, capturing solid debris, and cleaning and/or polishing dental instruments in the course of a dental procedure.

A principal object of the present invention is to provide a dental bib that is capable of protecting a patient's garments from liquid and/or solid debris during a dental procedure.

In one aspect, the present invention may comprise an apron further comprising an absorbent outer/front side layer constructed of one or more plies of an absorbent material, and an inner/back side impermeable layer constructed of one or more plies of an impermeable material. The outer/back side of the impermeable layer may be affixed to the inner/back side of the absorbent layer. The absorbent layer may capture liquid and/or solid debris while the impermeable layer prevents liquid and/or solid debris from penetrating through the apron and onto the garments of the patient.

Further objectives of the present invention are to capture solid debris generated during a dental procedure and to clean and/or polish dental instruments in the course of a dental procedure.

In another aspect, the present invention may comprise one or more windows of various shapes and sizes disposed about the front side of an apron, the windows comprising a gauze pad, captured between the absorbent and impermeable layers of the apron, and exposed by an aperture through the absorbent layer. The present invention may further comprise one or more pockets of various shapes and sizes disposed about the front side of an apron, the pockets comprising a gauze pocket captured between the absorbent layer and the impermeable layer of the apron, and exposed by an aperture through the absorbent layer. The pocket may be designed and configured such that, as the gauze pocket is captured beneath the aperture, an opening is formed into which a dental instrument may be inserted.

Other objects, aspects and advantages of the present invention will become readily apparent to those with skill in the art from the following figures, descriptions and claims. As will be appreciated by those with skill in the related art, the invention may be implemented in a plurality of equivalent embodiments. Such alternative embodiments, and their attendant objects, aspects and advantages, are within the scope of the present invention and, therefore, the examples set forth herein shall not be limiting.

BRIEF DESCRIPTION OF THE DRAWINGS

The nature of this invention, as well as all its objects, aspects and advantages, will become readily apparent and understood upon reference to the following detailed description when considered in conjunction with the accompanying drawings, in which like reference numerals designate like parts throughout the figures thereof, and wherein.

DETAILED DESCRIPTION OF THE INVENTION

The following description is provided to enable a person skilled in the relevant art to make and use the invention, and sets forth the best modes contemplated by the inventor of carrying out the invention. The present invention shall not be limited to the examples disclosed. Rather, the scope of the invention shall be as broad as the claims will allow.

Various inventive features are described below that may each be used independently of one another or in combination with other features. However, any single inventive feature may not address any of the disadvantages or objects discussed above, or might address only one of the disadvantages or objects discussed above. Further, one or more of the disadvantages or objects discussed above may not be fully addressed by any of the features described below.

Figure 1:
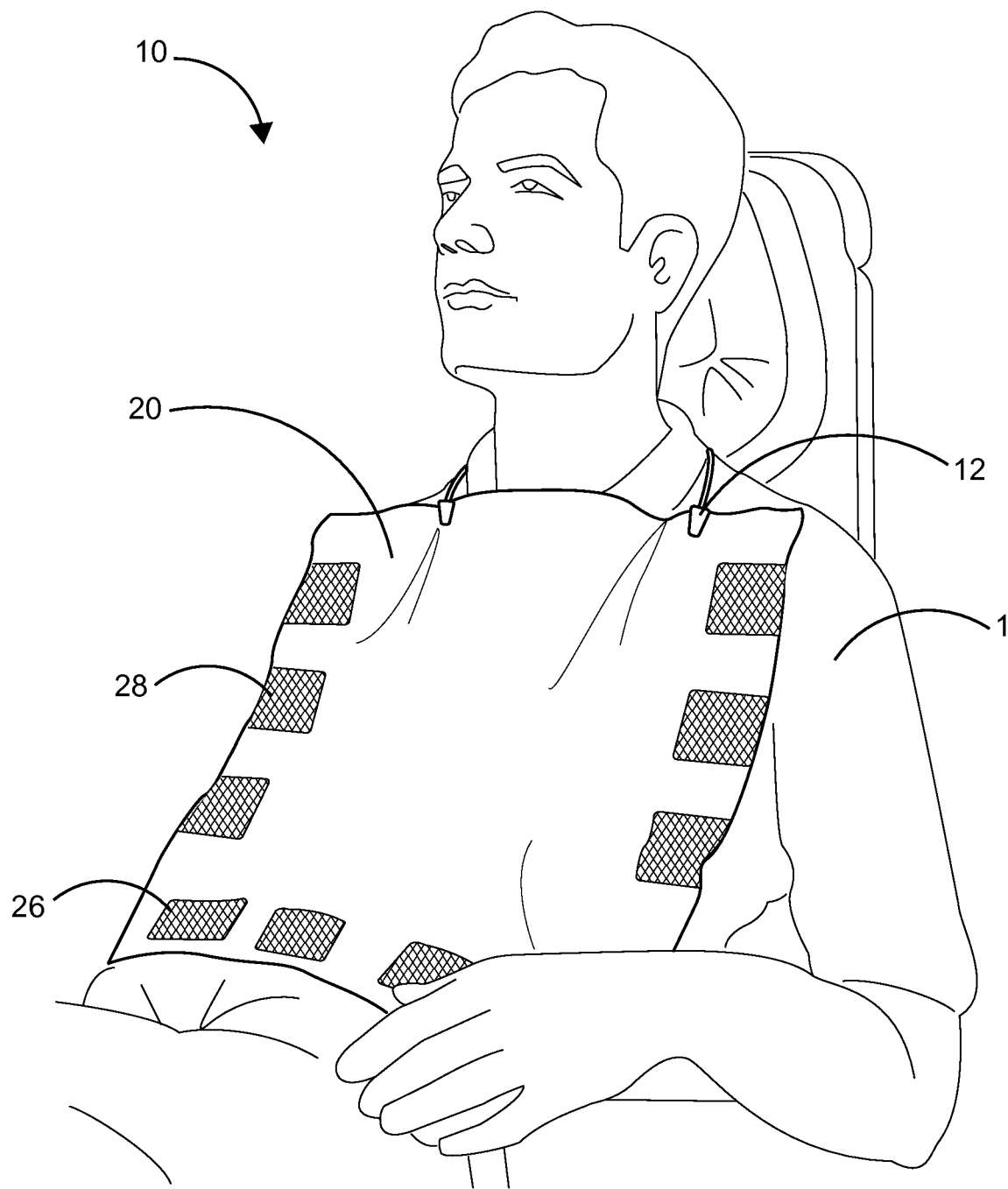
FIG. 1 presents a perspective view of a multi-purpose dental bib 10 in use, according to one exemplary embodiment of the present invention.

Referring now to the drawings, FIG. 1 presents a perspective view of a multi-purpose dental bib 10 in use by a patient 1, according to one exemplary embodiment of the present invention. In this exemplary embodiment, the multi-purpose dental bib 10 may comprise a generally rectangular apron 20, the apron 20 having a plurality of windows 26 and pockets 28. As illustrated in FIG. 1, the multi-purpose dental bib 10 may be held in place over the chest of a patient 1 by means of a bib clip 12. The bib clip 12 may be selected from the plurality of currently available designs, or a future design.

Figure 2:
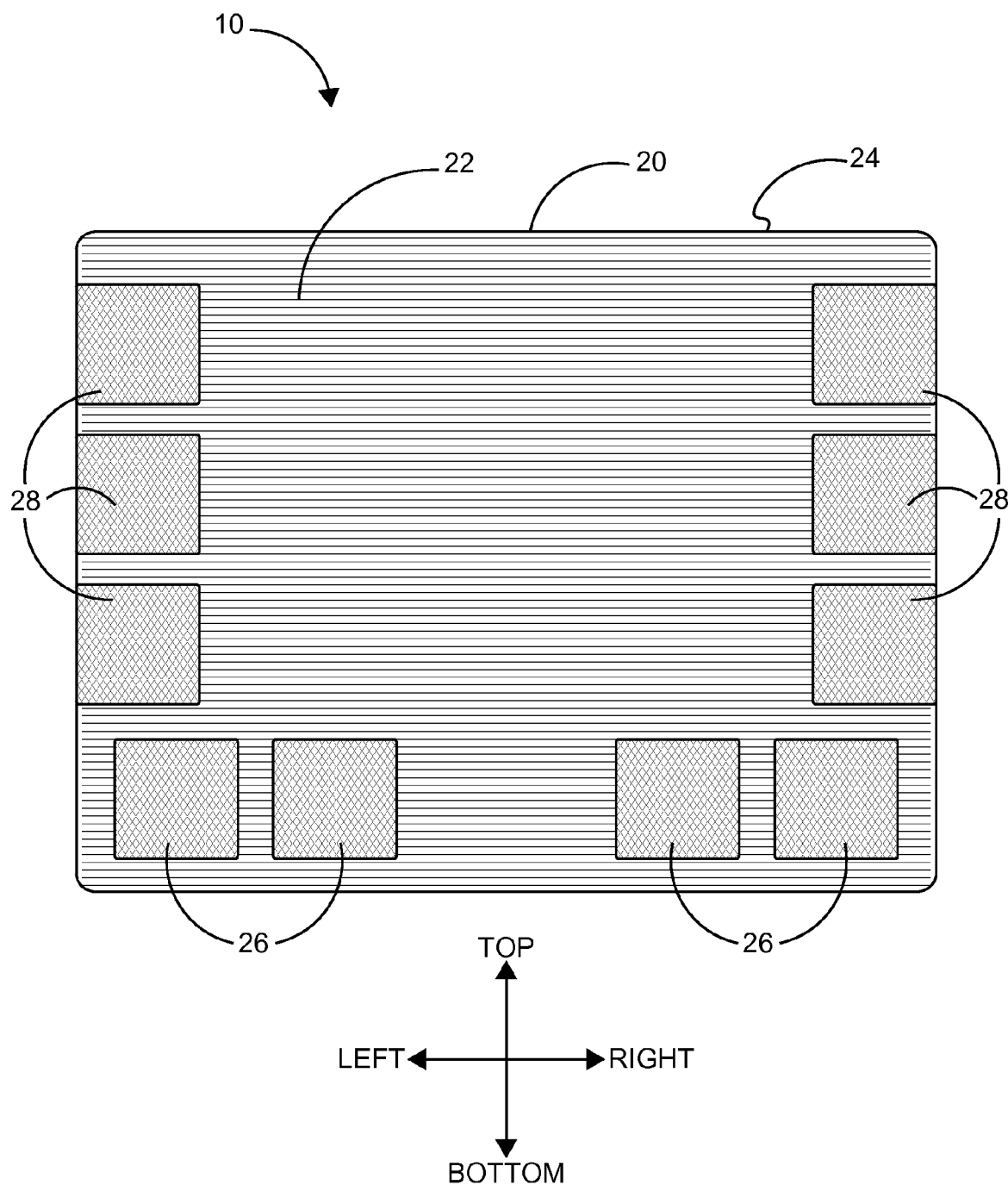
FIG. 2 presents a front view of the multi-purpose dental bib 10 of FIG. 1, according to one exemplary embodiment of the present invention.

FIG. 2 presents a front view of the multi-purpose dental bib 10 of FIG. 1, according to one exemplary embodiment of the present invention. The apron 20 may comprise an absorbent layer 22 on the front side of the apron 20, and an impermeable layer 24 on the back side of the apron 20.

The absorbent layer 22 may be designed to capture liquid and/or solid debris generated during a dental procedure. The absorbent layer 22 may comprise one or more sheets of an absorbent material. The one or more sheets of absorbent material may be constructed of any material that is appropriate to the intended function, such as a wood-pulp paper, cotton padding, or another natural or synthetic absorbent material, and may be similar in construction to a household paper towel or of a woven or quilted construction.

An impermeable layer 24 may be disposed over the back side of the absorbent layer 22. The impermeable layer 24 may be designed to protect the garments of a user 1 by preventing liquids from penetrating through the apron 20. The impermeable layer 24 may be made of any material that is appropriate to the intended function, such as a flexible plastic sheet or ply. The impermeable layer 24 may be affixed to the back side of the absorbent layer 22 by any practical means, such as heat bonding, an adhesive, or stitching.

A multi-purpose dental bib 10 may comprise one or more windows 26 and/or pockets 28, of various shapes and sizes, that may be integrated into the apron 20. The exemplary embodiment presented in FIG. 2 incorporates three pockets 28 on the left edge of the apron 20, three pockets 28 on the right side of the apron 20, and four windows 26 near the bottom edge of the apron 20.

Figure 3:
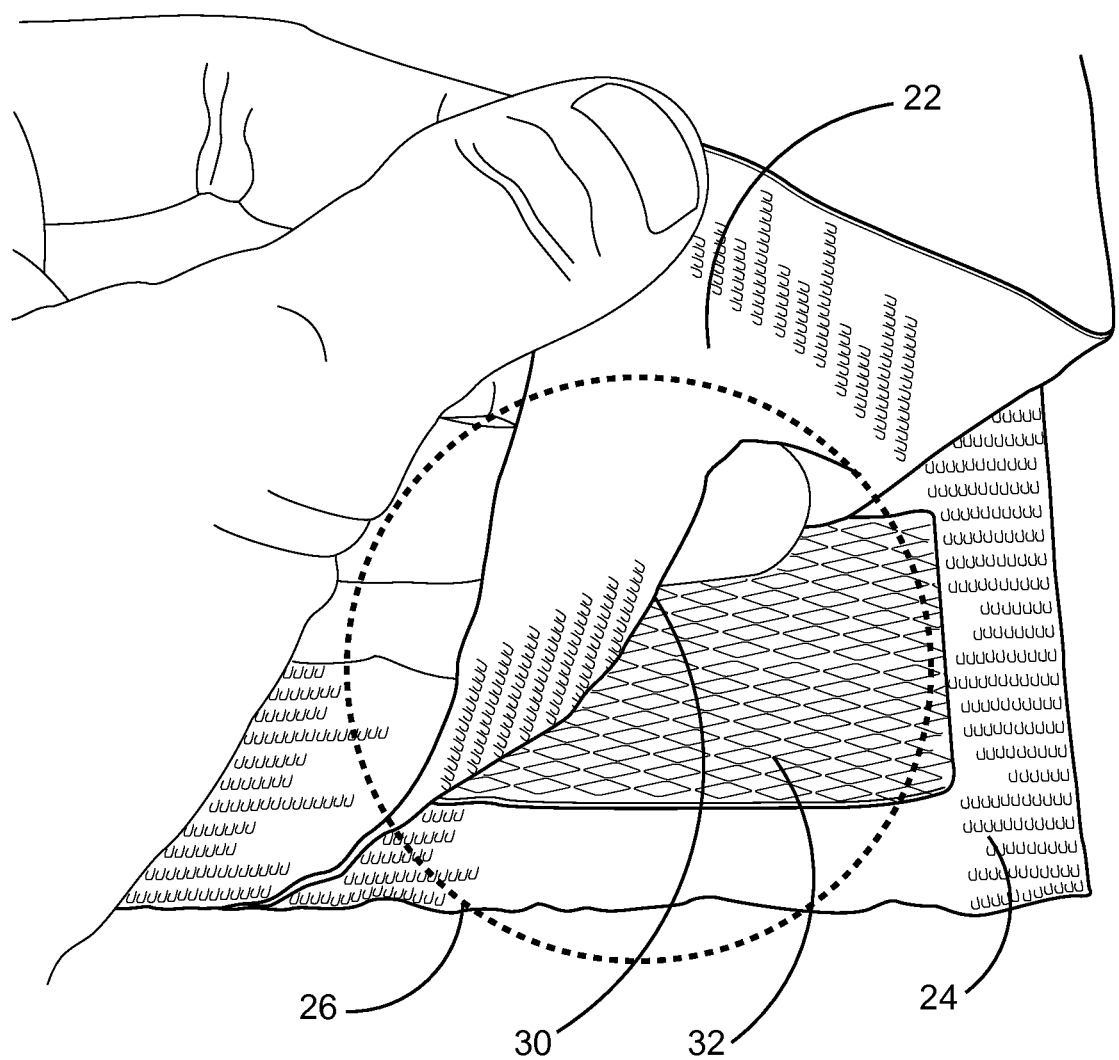
FIG. 3 presents a perspective detail view illustrating the construction of a window 26 of the multi-purpose dental bib 10 of FIG. 1, according to one exemplary embodiment of the present invention.

FIG. 3 presents a perspective detail view illustrating the construction of a window 26 of the multi-purpose dental bib 10 of FIG. 1, according to one exemplary embodiment of the present invention. An aperture 30 may be cut or otherwise formed through the absorbent layer 22 in a position on the apron 20 where a window 26 is desired. A gauze pad 32 may be positioned between the absorbent layer 22 and the impermeable layer 24 such that the gauze pad 32 may be essentially centered beneath the aperture 30. The impermeable layer 24 may then be attached to the back side of the absorbent layer 22, thereby capturing the gauze 32 beneath the aperture 30.

Typically, in medical and dental applications, gauze is a woven cotton material. However, the gauze pad 32 may be made of any material that is appropriate to the intended function, such as a wood-pulp paper, cotton padding, or another natural or synthetic absorbent material, and may be similar in construction to a household paper towel or of a quilted construction.

Figure 4A:
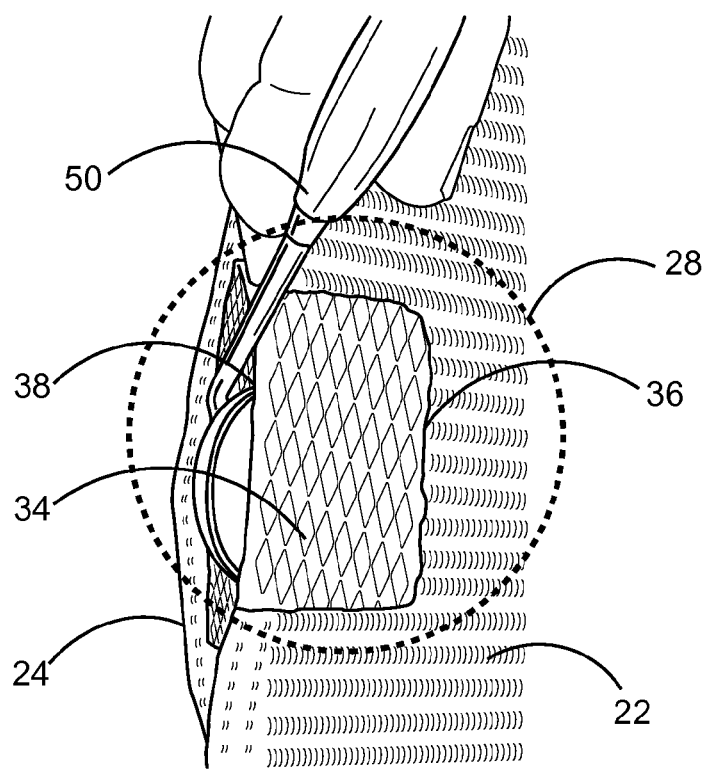
FIG. 4A presents a perspective detail view illustrating the construction and use of a pocket 28 of the multi-purpose dental bid 10 of FIG. 1, according to one alternative exemplary embodiment of the present invention.

FIG. 4A presents a perspective detail view illustrating the construction and use of a pocket 28 of the multi-purpose dental bid 10 of FIG. 1. An aperture 36 may be cut or otherwise formed through the absorbent layer 22 in a position on the apron 20 where a pocket 28 is desired. A gauze pocket 34 may be positioned between the absorbent layer 22 and the impermeable layer 24 such that the gauze pocket 34 may be essentially centered beneath the aperture 36. The impermeable layer 24 may then be attached to the back side of the absorbent layer 22, thereby capturing the gauze pocket 34 beneath the aperture 36.

The gauze pocket 34 may be constructed in a variety of alternative manners. In one exemplary embodiment, the gauze pocket 34 may be constructed of two gauze pads placed face-to-face against one another. In another alternative embodiment, the gauze pocket 34 may be made of a single gauze pad folded over upon itself.

The pocket 28 may be designed and configured such that, as the gauze pocket 34 is captured beneath the aperture 36, an opening 38 is formed into which a dental instrument may be inserted.

FIG. 4A illustrates the pocket 28 being used to clean a dental instrument, in this example a dental mirror 50.

Figure 4B:
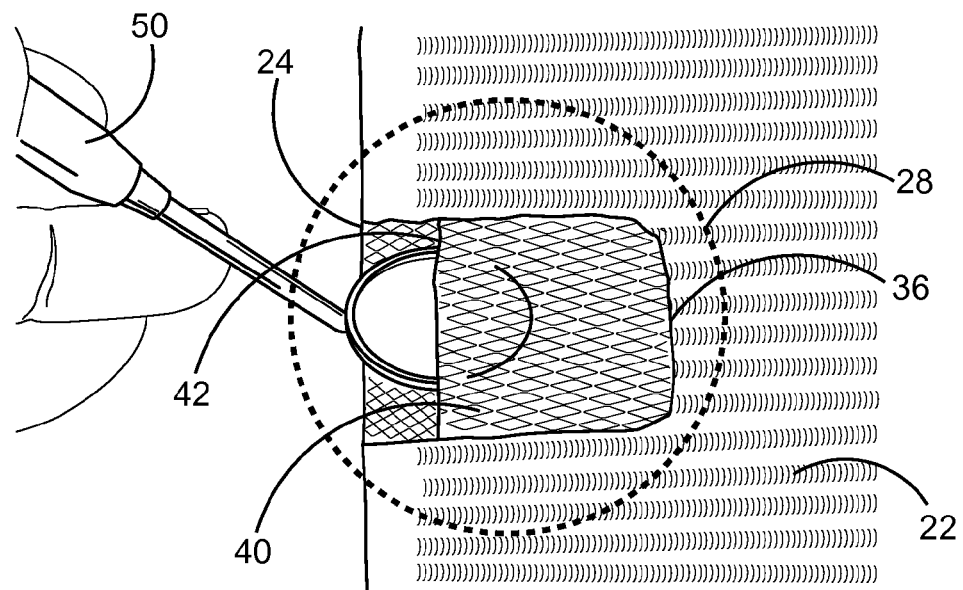
FIG. 4B presents a front detail view illustrating an alternative construction of a pocket 28 of the multi-purpose dental bib 10 of FIG. 1, according to an alternative exemplary embodiment of the present invention.

As will be apparent to one with skill in the related art, a pocket 28 may be constructed in a variety of manners, each of which is within the contemplated scope of the claims of this patent disclosure. FIG. 4B presents a front detail view illustrating one alternative construction of a pocket 28 of the multi-purpose dental bib 10 of FIG. 1, according to an alternative exemplary embodiment of the present invention. In this alternative embodiment, the pocket 28 may be constructed in the same manner as described and illustrated in FIG. 4A, except that the front-most gauze pad may be configured such that the outermost edge of the front-most gauze pad may be recessed from the edge of the apron 20. This construction facilitates the easy insertion of a dental tool, in this view a dental mirror 50, into the gauze pocket 40.

FIGS. 4A and 4B illustrate pockets 28 located proximal to an edge of an apron 20, according to exemplary embodiments of the present invention. In alternative embodiments, a pocket 28 may be located at any useful location on an apron 20. In an additional alternative embodiment, a pocket 28 may be configured without an aperture 36.

In alternative embodiments of the present invention, the windows 26 and pockets 28 may be configured, in size, shape, construction, and location on the apron 20, to accommodate a variety of tasks, including cleaning the face and/or mouth of a patient, capturing various types of debris, and cleaning dentistry tools of various shapes and sizes.

Alternative embodiments of the present invention may incorporate a means for holding the multi-purpose dental bid 10 in place, generally over a patient's chest, during dental procedures. These means may include adhesives, hook-and-loop fasteners, neck bands, clips, springs, or other practical means either currently known or to be defined in the future.

It is within the contemplated scope of the claims of this patent disclosure that the multi-purpose dental bib 10 may be useful in applications beyond dentistry, including medical applications, baby bibs, and adult bibs, among others.

As will be appreciated by those with skill in the related arts, the elements of the present invention may be modified, interchanged, separated or combined, or additional elements added without departing from the spirit of the invention. The invention may be practiced in alternative embodiments other than those illustrated in the Figures. Such modifications, combinations, additions and alternatives are within the contemplation of the present invention. The exemplary embodiments disclosed herein are not intended to limit the scope of this invention. Accordingly, the scope of the invention should be determined not by the embodiments illustrated, but by their legal equivalents, and shall be as broad as the claims will allow.

What is claimed is:

1. A multi-purpose dental bib, comprising:
   an apron, having a front side and a back side, comprising:
      an absorbent layer forming the outer layer of said front side of said apron, having a front side and a back side, said absorbent layer being constructed of one or more plies of an absorbent material; and
      an impermeable layer forming the outer layer of said back side of said apron, having a front side and a back side, said impermeable layer being constructed of one or more plies of an impermeable material, the surface of said front side of said impermeable layer being affixed to the surface of said back side of said absorbent layer; and
   one or more windows disposed about said front side of said apron, said one or more windows comprising a gauze pad captured between said absorbent layer and said impermeable layer, and generally centered behind and exposed by an aperture through said absorbent layer; and
   one or more pockets disposed about said front side of said apron, said one or more pockets comprising a gauze pocket captured between said absorbent layer and said impermeable layer such that an opening into said gauze pocket is formed.

2. A multi-purpose dental bib, comprising:
   an apron, having a front side and a back side, comprising:
      an absorbent layer forming said front side of said apron, having a front side and a back side, said absorbent layer being constructed of one or more plies of an absorbent material; and
      an impermeable layer forming said back side of said apron, having a front side and a back side, said impermeable layer being constructed of one or more plies of an impermeable material, the surface of said front side of said impermeable layer being affixed to the surface of said back side of said absorbent layer; and
   one or more pockets disposed about said front side of said apron, said one or more pockets comprising a gauze pocket captured between said absorbent layer and said impermeable layer such that an opening into said gauze pocket is formed; and wherein said gauze pocket is generally centered behind and exposed by an aperture through said absorbent layer.

3. The multi-purpose dental bib of claim 1 or claim 2, wherein said surface of said front side of said impermeable layer is affixed to said surface of said back side of said absorbent layer by a means selected from the group consisting of heat bonding, an adhesive, and stitching.

4. The multi-purpose dental bib of claim 1, wherein said gauze pocket is generally centered behind and exposed by an aperture through said absorbent layer.

5. The multi-purpose dental bib of claim 1 or claim 2, wherein said apron is configured in a generally-rectangular shape.

6. The multi-purpose dental bib of claim 1 or claim 2, wherein said apron is configured in a shape other than a generally-rectangular shape.

7. The multi-purpose dental bib of claim 1 or claim 2, further comprising a means of securing said multi-purpose dental bib in place over a patient.

8. The multi-purpose dental bib of claim 7, wherein said means of securing said multi-purpose dental bib is selected from the group consisting of adhesives, hook-and-loop fasteners, neck bands, clips, springs, and combinations thereof.

9. A method of making a multi-purpose dental bib, comprising:
   a. providing an apron, having a front side and a back side, comprising:
      an absorbent layer forming the outer layer of said front side of said apron, having a front side and a back side, said absorbent layer being constructed of one or more plies of an absorbent material; and
      an impermeable layer forming the outer layer of said back side of said apron, having a front side and a back side, said impermeable layer being constructed of one or more plies of an impermeable material, the surface of said front side of said impermeable layer being affixed to the surface of said back side of said absorbent layer; and
   b. disposing one or more windows about said front side of said apron, said one or more windows comprising a gauze pad captured between said absorbent layer and said impermeable layer, and generally centered behind and exposed by an aperture through said absorbent layer; and
   c. disposing one or more pockets about said front side of said apron, said one or more pockets comprising a gauze pocket captured between said absorbent layer and said impermeable layer such that an opening into said gauze pocket is formed.

10. The method of claim 9, wherein said surface of said front side of said impermeable layer is affixed to said surface of said back side of said absorbent layer by a means selected from the group consisting of heat bonding, an adhesive, and stitching.

11. The method of claim 9, wherein said gauze pocket is generally centered behind and exposed by an aperture through said absorbent layer.

12. The method of claim 9, wherein said apron is configured in a generally-rectangular shape.

13. The method of claim 9, wherein said apron is configured in a shape other than a generally-rectangular shape.

14. The method of claim 9, further comprising providing a means of securing said multi-purpose dental bib in place over a patient.

15. The method of claim 14, wherein said means of securing said multi-purpose dental bib is selected from the group consisting of adhesives, hook-and-loop fasteners, neck bands, clips, springs, and combinations thereof.

* * * * *